US006258366B1

(12) United States Patent
Gedouin et al.

(10) Patent No.: US 6,258,366 B1
(45) Date of Patent: Jul. 10, 2001

(54) METHOD OF PREPARING A COSMETIC PRODUCT INTENDING TO PROTECT THE SKIN AGAINST ATTACKS RESULTING FROM POLLUTION OF THE AMBIENT AIR

(75) Inventors: Antoine Gedouin; Romuald Vallee, both of St. Malo (FR)

(73) Assignee: Codif International S.A., Sant-Malo Cedex (FR)

( * ) Notice: Subject to any disclaimer, the term of this patent is extended or adjusted under 35 U.S.C. 154(b) by 0 days.

(21) Appl. No.: 09/337,274

(22) Filed: Jun. 22, 1999

(30) Foreign Application Priority Data

Jun. 22, 1998 (FR) ................................... 98 08034

(51) Int. Cl.⁷ ............................... A61K 6/00; A61K 7/00
(52) U.S. Cl. ............................ 424/401; 424/400; 424/59
(58) Field of Search ..................................... 424/400, 401, 424/404, 405, 59, 60, 78.02, 78.03, 78.04

(56) References Cited

U.S. PATENT DOCUMENTS 5,416,205 * 5/1995 della Valle et al. ................... 514/54
5,776,445 * 7/1995 Cohen et al. ...................... 424/78.04

FOREIGN PATENT DOCUMENTS

| 18 07 152 | 5/1970 | (DE) . |
| 30 17 221 | 11/1980 | (DE) . |
| 1 345 295 | 3/1964 | (FR) . |

OTHER PUBLICATIONS

Patent Abstracts of Japan, vol. 10, No. 262 (C–371) [2318], Sep. 6, 1986, & JP 61 087614 A (Daiichi Seimo), May 6, 1986.

* cited by examiner

Primary Examiner—Dameron L. Jones
(74) Attorney, Agent, or Firm—Lowe Hauptman Gilman & Berner

(57) ABSTRACT

The use of a depolymerized sodium aliginate composition as a cosmetic preparation that has the ability to protect the skin of the wearer against harmful effects of atmosphere pollution.

21 Claims, No Drawings

METHOD OF PREPARING A COSMETIC PRODUCT INTENDING TO PROTECT THE SKIN AGAINST ATTACKS RESULTING FROM POLLUTION OF THE AMBIENT AIR

The present invention concerns a method of preparing a product intended for cutaneous protection against attack resulting from pollution of the ambient air and a method of protecting the skin against such attack.

Human beings are subjected daily to ever increasing pollution. Changes in the ecosystem, reinforced by overpopulation and excessive human activity, cause high pollution levels. This situation was largely generated initially by our industrial activity. There has been a change in the environment itself, with a reduction in the stratospheric ozone layer, an intensified greenhouse effect giving rise to global warming. The triposhere is gradually becoming an oxiding medium ($O_3$, NOx, metals).

To all this it is necessary to add cigarette fumes which impinge on facial skin. These cause a reduction in hydration and oxygenation.

The mechanisms by which pollution and its effects act on the skin remain poorly known. It is known however that tobacco causes right-angled wrinkles at the edge of the lips, numerous furrows on the checks and chin an a greyish complexion.

In addition, urban pollution causes acidification of the skin, disturbance of hydration with a concomitant increase in the transepidermal water loss, an increase in skin flaking and a reduction in skin flexibility.

As a protective barrier between the body and the external environment, it is the skin which is confronted with the harmful effects of pollution.

The purpose of the invention is to propose a method of protecting the skin which considerably reduces the effect of this pollution on the skin.

To do this, a method according to the invention consists of using the product of the enzymatic depolymerisation of a sodium alginate extracted from an alga, for example a brown alga. The alginate in question is a linear copolymer consisting of sodium $\alpha$-L-guluronate and sodium $\beta$-D-mannuronate bonded at positions 1,4 in homogeneous alternating blocks. For this enzymatic depolymerisation, an enzyme of the mannuronate lyase type, preferably an alginate lyase, has, for example, been used.

This enzyme, obtained by bacterial fermentation, makes it possible to depolymerise, by $\beta$-elimination, the alternating blocks of the sodium alginate molecule. In addition, the aforementioned enzyme very quickly reduces the viscosity of the sodium alginate solution at the end of said depolymerisation step.

For example, the product used is prepared as follows. The alga extract consisting of sodium alginate is first of all solubilised for one hour at a concentration of 5%. The solubilised alginate extract is then subjected to an enzymatic depolymerisation at a temperature of 25° C. for four hours, by means of a lyase alginate known as AL 951. In addition, the ratio by weight of enzyme to alginate is 0.01% and the pH of the mediums is 7.5.

The oligoalginates obtained by this depolymerisation are formed by the linking of two uric acids: mannuronic acid and guluronic acid.

The said degree of polymerisation of the product used is advantageously 80, measured by the so-called "conjugated double bond determination" method. The mean molecular weight in number is approximately twenty thousand daltons, measured by the so-called "reducing sugars determination" method of Somogyi-Nelson.

The present invention also concerns a method for producing a cosmetic product intended for protecting the skin against pollution attack. It is characterised in that it also was an enzymatic depolymerisation product of a sodium alginate extracted from an alga of the type described above.

It is shown below that the use of such a depolymerisation product actually has the intended skin-protection effect.

It first of all enables the human epidermis to be protected. To demonstrate this, reconstructed human epidermes were incubated for 30 minutes at 37° C., some without the deposition of product, referred to as the controls, others after deposition on their surface of product which had been previously diluted to 1% by volume.

The epidermes were subjected to a pro-radical stress caused by exposure of one hour in the presence of cigarette fumes. They were then incubated for 24 hours at 37° C.

The viability of the keratinocytes was evaluated qualitatively by the morphological observation of histological sections. The viability of the keratinocytes was evaluated quantitatively by the reduction in MTT (dimethylthiazole diphenyltetrazolium bromide) and a spectrophotometric reading.

It was thus found that, in the absence of fumes, the epidermes were intact. The cellular viability was good. The presence of cells in apoptosis was exceptional. The product was not toxic for the epidermal cells. Viability was even increased by 20%.

After exposure to cigarette fumes, in the absence of product, viability was reduced by 40% (see table below). It was remarked that cells in apoptosis appear in the granular layer. On the other hand, with product present the cellular viability decreased by only 10% after exposure to cigarette fumes (see table below).

It can be deduced therefrom that the product protects the epidermes from cigarette fumes.

|  | Epidermis without product | | Epidermis with product at 0.1% |
| --- | --- | --- | --- |
|  | Without fumes | With fumes | With fumes |
| Number of cells (in milliunits of DO) | 559 | 374 | 592 |
|  | 658 | 354 | 506 |
| MEAN | 608 | 364 | 549 |
| % of control | 100 | 60 | 90 |

It also affords protection of fibroblasts. To demonstrate this, cultures of human dermis fibroblasts were prepared, which were incubated for 30 minutes at 37° C., some in a culture medium without product (the control), others in a culture medium with a 0.1% dilution of the product. Some fibroblasts were then subjected to a pro-radical stress caused by an exposure of one hour in the presence of cigarette fumes. They were then incubated for 24 hours at 37° C.

The viability of the fibroblasts was evaluated by the reduction in the MTT (dimethylthiazole diphenyltetrazolium bromide) and a spectrophotometric reading.

In the absence of fumes, the viability of the fibroblasts was good. The product was not toxic for the cells.

After exposure to cigarette fumes, the cellular viability decreased by 47% (see table below). With product present, the cellular viability decreased only by 31% (see table below).

The product therefore protects the dermis cells from cigarette fumes.

|  | Fibroblasts without product | | Fibroblasts with product at 0.1% |
| --- | --- | --- | --- |
|  | Without fumes | With fumes | With fumes |
| Number of cells (in milliunits of DO) | 155 | 55 | 123 |
|  | 149 | 95 | 101 |
|  | 167 | 99 | 100 |
| MEAN | 157 | 83 | 108 |
| % of control | 100 | 53 | 69 |

By virtue of its high degree of polymerisation of 80, the product remains on the surface of the skin. It can protect the epidermis against heavy metals from the environment. This effect has been shown for two metals, lead and cadmium.

The product, diluted to 5%, was tested, in solutions containing lead and cadmium, at three different concentrations, under stirring for one hour, and under the same conditions as the surface of the skin (32° C. and pH 5.5), and then the quantity of metals chelated in these solutions was measured.

The following table shows that the chelation of these two metals by the product is effected with high affinity.

|  | Concentration of $Pb(NO_3)_2$ (mg/kg) | | Concentration of $Cd(NO_3)_2$ (mg/kg) | |
| --- | --- | --- | --- | --- |
|  | 20 | 94 | 20 | 51 |
| % chelation | 87 | 84 | 98 | 80.5 |

What is claimed is:

1. Method of preparing a cosmetic product, intended to protect the skin against attacks by polluted ambient air, comprising enzymatically depolymerizing a sodium alginate extracted from alga to form a depolymerization product, and formulating said depolymerization product into a cosmetic formulation.

2. Method of preparing a cosmetic product as claimed in claim 1 comprising depolymerizing an extract of alga, that has been solubilised at a concentration of 5%,, for four hours at a temperature of 25° C. and at a pH of 7.5, by an alginate lyase AL 951.

3. Method of protecting the skin against attacks by poluted ambient air, comprising applying and effective amount of a product of the enzymatic depolymerisation of a sodium alginate extracted from alga to the skin.

4. Method of protecting the skin against attacks by polluted ambient air as claimed in claim 3, comprising using an extract of alga solubilized at a concentration of 5% that has been depolymerized by an alginate lyase AL 951 at a temperature of 25° C. for four hours and at a pH of 7.5.

5. Preparation method according to claim 1, wherein said alga is a brown alga.

6. Method according to claim 1, wherein said alginate comprises a linear copolymer comprising sodium α-L-guluronate and sodium β-D-mannuronate.

7. Method according to claim 1, wherein said depolymerisation is carried out using a mannuronate lyase enzyme.

8. Method according to claim 1, wherein said depolymerisation product has a degree of polymerisation of approximately 80.

9. Method of protecting the skin against attacks resulting form contact with ambient air, comprising applying to the skin a cosmetic product produced by a method of claim 1.

10. A depolymerized oligoalginate comprising linked mannuronic acid and guluronic acid moieties.

11. A depolymerized oligoalginate as claimed in claim 10 having a degree of polymerization, as measured by conjugated double bond determination, of about 80, and a number average molecular weight, measured by reducing sugars determination, of about 20,000 daltons.

12. An oligoalginate as claimed in claim 10 consisting essentially of linked mannuronic acid and guluronic acid moieties.

13. An oligoalginate as claimed in claim 10 made by depolymerizing a substantially linear copolymer comprising α-L-guluronate and β-D-mannuronate.

14. An oligoalginate as claimed in claim 13 wherein said substantially linear polymer comprises α-L-guluronate and β-D-mannuronate bonded at the 1,4 position in substantially homogeneous alternating blocks.

15. A depolymerized oligoalginate as claimed in claim 13 wherein said depolymerization has been carried out in the presence of an effective amount of a mannuronic lyase enzyme.

16. An oligoalginate as claimed in claim 15 wherein said mannuronic lyase enzyme comprises an alginate lyase.

17. A cosmetic product comprising an oligoalginate as claimed in claim 10 and a dermatologically acceptable carrier therefore.

18. A cosmetic product comprising an oligoalginate as claimed in claim 10.

19. A cosmetic product comprising an oligoalginate as claimed in claim 13 and a physiologically acceptable carrier therefore.

20. A cosmetic product comprising an admixture of about 1% by weight of an oligoalginate as claimed in claim 10 and the remainder a dermatologically acceptable carrier therefore.

21. Method according to claim 7 wherein said depolymerisation is carried out using an alginate lyase obtained by bacterial fermentation.

* * * * *